United States Patent [19]

Vanderheyden et al.

[11] Patent Number: 5,393,512

[45] Date of Patent: Feb. 28, 1995

[54] STABLE THERAPEUTIC RADIONUCLIDE COMPOSITIONS AND METHODS FOR PREPARATION THEREOF

[76] Inventors: Jean-Luc Vanderheyden, 2418 W. Lynn, Seattle, Wash. 98199; Alan R. Fritzberg, 16703 74th Place West, Edmonds, Wash. 98020; Joseph E. Bugaj, 13331 28th Ave. SE., Bothell, Wash. 98012; Fu-Min Su, 3245 NE. 100th St., Seattle, Wash. 98125; Prasanna Venkatesan, 12631 NE. 130th Ct., Apt. D308, Kirkland, Wash. 98034

[21] Appl. No.: 124,359

[22] Filed: Sep. 20, 1993

Related U.S. Application Data

[63] Continuation of Ser. No. 810,556, Dec. 20, 1991, abandoned, which is a continuation of Ser. No. 441,372, Sep. 22, 1989, abandoned, which is a continuation-in-part of Ser. No. 65,011, Jun. 19, 1987, Pat. No. 4,897,255, which is a continuation-in-part of Ser. No. 817,321, Jan. 9, 1986, abandoned, which is a continuation-in-part of Ser. No. 692,000, Jan. 14, 1985, abandoned.

[51] Int. Cl.⁶ ..................... A61K 43/00; A61K 49/02
[52] U.S. Cl. ................................. 424/1.53; 424/1.11; 424/1.69; 424/1.65
[58] Field of Search .................. 424/1.45, 1.69, 1.49, 424/1.53, 1.11

[56] References Cited

U.S. PATENT DOCUMENTS

| | | | |
|---|---|---|---|
| 4,233,000 | 11/1980 | Fawzi | 424/1.1 |
| 4,364,920 | 12/1982 | Winchell | 424/1.1 |
| 4,416,865 | 11/1991 | Rhodes et al. | 424/1.1 |
| 4,440,738 | 4/1984 | Fawzi et al. | 424/1.1 |
| 4,510,125 | 4/1985 | Grogg et al. | 424/1.1 |
| 4,645,660 | 2/1987 | Takahashi et al. | 424/1.1 |
| 4,652,440 | 3/1987 | Paik et al. | 424/1.1 |
| 4,707,353 | 11/1987 | Bugaj et al. | 424/1.1 |
| 4,793,987 | 12/1988 | Henderson et al. | 424/1.1 |
| 4,808,705 | 2/1989 | Ferris | 530/391 |
| 4,812,557 | 3/1989 | Yasushi et al. | 530/351 |
| 4,837,003 | 6/1989 | Nicolotti | 424/1.1 |
| 4,849,511 | 7/1989 | Verbruggen | 534/14 |
| 4,880,615 | 11/1989 | Charleson | 424/1.1 |
| 4,897,255 | 1/1990 | Fritzberg et al. | 424/1.1 |
| 4,917,878 | 4/1990 | Thakur | 424/1.1 |
| 4,935,222 | 6/1990 | Deutsch et al. | 424/1.1 |
| 4,980,147 | 12/1990 | Fritzberg et al. | 424/1.1 |
| 5,021,235 | 6/1991 | Pipes | 424/1.1 |
| 5,053,493 | 10/1991 | Pak et al. | 530/402 |
| 5,128,119 | 5/1992 | Griffiths et al. | 424/1.1 |

FOREIGN PATENT DOCUMENTS

| | | | |
|---|---|---|---|
| 0250966 | 1/1988 | European Pat. Off. | |
| 0280209 | 8/1988 | European Pat. Off. | C12N 15/00 |
| 0284071 | 9/1988 | European Pat. Off. | C07K 15/00 |
| 0306168 | 3/1989 | European Pat. Off. | C07B 59/00 |
| 0315188 | 5/1989 | European Pat. Off. | A61K 49/02 |
| 2309215 | 11/1976 | France | A61K 29/00 |
| 2527928 | 12/1983 | France | A61K 43/00 |
| 2331550 | 1/1974 | Germany | C08H 1/00 |
| 9013530 | 11/1990 | WIPO | |

OTHER PUBLICATIONS

Kishore et al., "Autoradiolysis of Iodinated Monoclonal Antibody Preparations"; pp. 457–459 Nucl. Med. Biol., vol. 13.

Frie et al., "Ascorbate is an Outstanding Antioxidant in Human Blood Plasma", Proc. Natl. Acad. Sci., vol. 86, pp. 6377–6381.

Berger, Ralph, "Radical Scavengers and the Stability of $^{99m}$Tc-Radiopharmaceuticals", Int. J. Appl. Radiat. Insot., vol. 33 pp. 1341–1344.

Mather, Stephen J., "Labelling monoclonal antibodies with Yttrium-90"; Fur. J. Nucl. Med (1989), 15:307–312.

Deutsch et al. "The Chemistry of Rhenium+Technetium", Nucl Med Biol, No. 4, pp. 465–477, 1986.

*Primary Examiner*—Robert L. Stoll
*Assistant Examiner*—John M. Covert

[57] ABSTRACT

Stable therapeutic radionuclide compositions comprising, for example, $^{186}$Re, $^{188}$Re and $^{131}$I stably bound to a proteinaceous targeting moiety and suitable for human in vivo administration are disclosed. Stabilizing agents preferably comprise antioxidants and challenging agents, and combination of HSA with an antioxidant and/or challenging agent provides enhanced long term stability. Ascorbic acid is an especially preferred stabilizing agent, which provides stability of therapeutic radionuclide compositions at levels of at least about 90% for several hours up to several days.

12 Claims, No Drawings

STABLE THERAPEUTIC RADIONUCLIDE COMPOSITIONS AND METHODS FOR PREPARATION THEREOF

This is a continuation of application Ser. No. 07/810,556, filed Dec. 20, 1991, now abandoned, which is a continuation of application Ser. No. 07/441,372, filed Sep. 22, 1989, now abandoned, which is a continuation-in-part of application Ser. No. 07/065,011, filed Jun. 19, 1987, now U.S. Pat. No. 4,897,255, which is a continuation-in-part of application Ser. No. 06/817,321, filed Jan. 9, 1986, now abandoned, which is a continuation-in-part of application Ser. No. 06/692,000, filed Jan. 14, 1985, now abandoned.

FIELD OF THE INVENTION

The present invention relates generally to stable therapeutic radionuclide-labeled compositions, and to methods for preparation and stabilization thereof.

BACKGROUND ART

Radio-labeled compositions are important tools in medical diagnosis and treatment. Such compositions may be employed in a variety of techniques, including the diagnosis of deep venous thrombi, the study of lymph node pathology, and the detection, staging and treatment of neoplasms. When employing radio-labeled compositions for in vivo diagnostic or therapeutic applications, it is important that the radionuclide preferentially localize in target tissues. Therefore, radionuclides are generally coupled to targeting agents to provide preferential binding to or absorption by the particular cells or tissue(s) of interest. Radionuclides are typically bound to a chelating agent, and the chelating agent is coupled to a targeting moiety to provide a radio-labeled composition capable of binding selectively to a specified population of target cells or tissue(s).

Radionuclides such as $^{99m}$Tc, $^{131}$I, $^{123}$I, $^{117m}$Sn, $^{111}$In, $^{113}$In, $^{97}$Ru, $^{76}$Br, $^{77}$Br, $^{203}$Pb, $^{18}$F, $^{67}$Ga, $^{89}$Zr, and $^{64}$Cu have been proposed for use as diagnostic imaging agents. $^{99m}$Tc is one particularly promising diagnostic imaging agent. Technetium-99m is produced commercially in generators by eluting a saline solution through a matrix containing molybdenum. The metastable technetium isotope in such eluates is found in the chemically stable, oxidized pertechnetate form $^{99m}$TcO$_4^-$. Because pertechnetate-$^{99m}$Tc has a valence state of +7, it will not complex with the most commonly used carriers for radionuclide tissue imaging. $^{99m}$TcO$_4^-$ is therefore commonly reduced to lower oxidation states, such as $^{99m}$TcO$^{3+}$ and $^{99m}$TcO$_2^+$ by admixing $^{99m}$TcO$_4^-$ isotonic saline solutions with technetium reductants such as stannous, ferrous and chromous salts and acids such as sulfuric and hydrochloric.

Therapeutic radionuclides such as $^{32}$P and $^{131}$I have been used to treat malignancies such as polycythemia vera and metastatic thyroid carcinoma, respectively. A variety of radionuclides may be useful for therapeutic applications, including alpha emitters, low, medium and high range beta emitters, and radionuclides which act through electron capture and/or internal conversion (auger electrons). Sources of alpha emitters, such as $^{211}$At, are relatively limited, while beta sources are far more plentiful. Numerous medium range beta sources, including $^{47}$Sc, $^{67}$Cu, $^{131}$I, $^{153}$Sm, $^{109}$Pd, $^{105}$Rh, and $^{186}$Re, have been proposed for therapeutic applications. $^{131}$I is frequently used for antibody-directed therapy, but it suffers from increased non-target toxicity due to the abundance of high energy gamma rays emitted therefrom and dehalogenation. Concerns related to dehalogenation of $^{131}$I therapeutic compositions may be substantially reduced by attachment of para-iodophenyl moieties as taught in European Patent Application Publication 0 203 764. Long range beta particle sources potentially suitable for therapeutic administration include $^{32}$P, $^{90}$Y and $^{188}$Re. $^{186}$Re and $^{188}$Re also emit gamma radiation at essentially the same energy as the gamma emission of $^{99m}$Tc, which allows the biodistribution of rhenium radiopharmaceuticals to be readily monitored using conventional gamma camera instrumentation.

Therapeutic compositions comprising beta emitting radionuclides may undergo radiolysis during preparation and/or in vitro storage. During radiolysis, emissions from the radionuclide attack other constituents of the complex or compound, or other compounds in proximity, which results in inter- and intra-molecular decomposition. Radiolytic decay poses serious safety concerns, since decomposition or destruction of the radionuclide chelate, the radionuclide chelate-targeting agent linkage, or the specificity conferring portion of the targeting agent results in non-targeted radioactivity. Radioactivity which is not linked to a functional targeting agent will accumulate in non-target tissues, and decomposition of the radionuclide composition prior to or during administration dramatically decreases the targeting potential and thus increases the toxicity of the therapeutic radionuclide composition. It is thus important, particularly with respect to therapeutic radionuclide preparations intended for in vivo administration, to ensure that the radioactive moiety is stably linked to the targeting moiety, and the specificity of the targeting agent is preserved.

$^{99m}$Tc and radioactive rhenium, including $^{186}$Re and $^{188}$Re, are Group VIIA congeners. Rhenium and technetium share many physical properties, such as size, shape, dipole moment, formal charge, ionic mobility, lipophilicity, and the like. For example, many chelating agents which have been developed and/or used for $^{99m}$Tc are also suitable for use with rhenium radionuclides. Little is known, however, about the properties of radioactive rhenium therapeutic compositions, since research involving rhenium radionuclides is still at a relatively preliminary stage. Perrhenate (ReO$_4^-$), which is formed as a result of unstable rhenium complexes in lower oxidation states moving to higher oxidation states, is the primary decomposition product of rhenium radionuclide compositions.

E. Deutsch, et al., in an article entitled "The Chemistry of Rhenium and Technetium as Related to the Use of Isotopes of these Elements in Therapeutic and Diagnostic Nuclear Medicine", Nucl. Med. Biol., Vol 13, No. 4, pp. 465–477, 1986, present a review of the comparative properties of technetium and rhenium radionuclides and their applications to therapeutic and diagnostic nuclear medicine. Technetium and rhenium both exhibit redox chemistry, and pertechnetate and perrhenate, respectively, must be converted to lower oxidation states prior to chemical reaction with chelating agents. The chemistry of rhenium is sufficiently different from that of technetium, however, that the development of rhenium radiopharmaceuticals often cannot be predicated on the known chemistry and biological behavior of $^{99m}$Tc radiopharmaceuticals. The most relevant of the chemical differences may be that rhenium complexes are thermodynamically more stable in their higher oxidation states, in the form of perrhenate, than are their technetium analogs. Rhenium compositions are therefore more difficult to reduce than their technetium analogs, and reduced rhenium radiopharmaceuticals tend to be re-oxidized back to perrhenate more readily than analogous technetium radiopharmaceuticals are re-oxidized back to pertechnetate.

Deutsch et al. prepared rhenium radionuclide analogs of $^{99m}$Tc bone-seeking radiopharmaceuticals, including $^{186}$Re(Sn)-HEDP [HEDP=(1-hydroxyethylidene)diphosphonate], and [$^{186}$Re(DMPE)$_3$]+, [DMPE=1,2-bis(dimethylphosphino)ethane]. In these conjugates, the radionuclide is coupled directly to the inorganic diphosphonate targeting agent. The researchers compared the properties of rhenium preparations, and their in vivo biodistribution, with the corresponding $^{99m}$Tc analogs. Decomposition of the rhenium complexes to perrhenate was much more pervasive than decomposition of the technetium analogs to pertechnetate. The presence of perrhenate was attributed to incomplete reduction of perrhenate in the original synthesis, reoxidation of rhenium complexes to perrhenate by adventitious oxygen, and disproportionation of the rhenium radionuclide complex. Deutsch et al. found that chromatographic purification of the rhenium radionuclide preparations was essential to provide satisfactory purity levels. Ascorbic acid was suggested for use as an antioxidant, but the purified preparation still required anaerobic handling and was used as quickly as possible after it was generated. Deutsch et al. concluded that the successful development of a $^{186}$Re(Sn)-HEDP radiopharmaceutical for the palliative treatment of metastatic cancer to bone analogous to the $^{99m}$Tc(Sn)-HEDP radiopharmaceutical used to diagnose metastatic bone cancer depends upon the ability to control the redox properties of rhenium radionuclides.

Stabilization of therapeutic radionuclide compositions is a recurrent challenge in the field of therapeutic radionuclide conjugates. Stabilization of radioactive compositions is generally more difficult to achieve without loss of desired properties than stabilization of other, structurally similar chemical compositions. Therapeutic radionuclide compositions behave differently from and are generally less stable than diagnostic radionuclide compositions.

Since decomposition of therapeutic radionuclide compositions is generally so rapid over time, clinical radionuclide preparations are prepared immediately prior to administration. This requires that the treating facility have the laboratory facilities and skilled technicians necessary for manipulating radioactive materials, which generally involves chelating the radionuclide and conjugating the radionuclide to the targeting moiety. Additionally, significant resources are devoted to preparing patients so they may undergo treatment immediately after purification of the therapeutic radionuclide composition. If the preparation is contaminated or does not meet the purity requirements, the patient must either wait a considerable time period for a second preparation, or undergo the trauma of waiting yet a longer interim period. Such delays are traumatic to the patient and waste valuable facility and personnel resources. Effective in vitro stabilization of therapeutic radionuclide compositions would permit more centralized, controlled preparation of therapeutic radionuclide compositions, and thereby provide greater access to therapeutic compositions having higher purity levels.

SUMMARY OF THE INVENTION

The methods of the present invention provide stabilization of therapeutic radionuclide compositions by addition of an effective amount of a stabilizing agent. Effective in vitro stabilization of therapeutic radionuclide compositions is critical when the composition is intended for in vivo patient administration. Purity levels of radionuclide compositions are typically measured as the ratio of radionuclide bound to targeting moiety to the total radionuclide in the preparation. Limitations relating to the purity of radionuclide preparations which can be administered to humans are strictly observed. In general, the preparation is at least 90% pure, and it is preferably at least 95% pure. High purity levels are, of course, preferable, and purity levels below about 90% are generally considered unsuitable for in vivo human administration.

Stabilizers for use with therapeutic radio-labeled compounds desirably possess the following characteristics: they are toxicologically acceptable under conditions of use; they are suitable for in vivo administration; they do not interfere with delivery of the compound to the target cells or tissue(s); and they stabilize the product for reasonable periods during preparation and storage prior to use. One of the important benefits of the stabilizing agents employed in the present invention is that they permit in vitro storage of prepared, purified radio-labeled compositions for at least several hours and up to several days, while maintaining acceptable purity levels.

As used herein, the term "therapeutic radionuclide composition" means a radionuclide having therapeutic properties complexed or otherwise associated with a targeting moiety. The therapeutic radionuclide compositions of the present invention preferably incorporate therapeutic radionuclides which exhibit redox chemistry, such as rhenium radionuclides, and/or are prone to decomposition as a result of radiolysis products such as peroxides and free radicals such as $^{131}$I. Therapeutic radionuclide compositions of the present invention preferably comprise beta radiation emitting isotopes such as $^{186}$Re, $^{188}$Re, and the like, which may be complexed or associated with various other constituents, such as chelating agents and targeting moieties. Therapeutic radioimmunoconjugates comprising a therapeutic radionuclide bound to a chelating agent, which is in turn linked to a proteinaceous targeting moiety, are especially preferred. The rhenium radionuclides, $^{186}$Re and $^{188}$Re, which emit both beta and gamma radiation, are preferred for use in stable therapeutic compositions according to the present invention.

A stabilizing agent is introduced to the therapeutic preparation, which is preferably in aqueous solution suitable for in vivo administration to human patients. Suitable stabilizing agents include antioxidants such as ascorbic acid, gentisic acid, and functionally similar compounds, as well as challenging agents such as DTPA [DTPA=diethylenetriamine pentaacetate], EDTA [EDTA=ethylene diaminetetra acetate], and the like, which are acceptable for in vivo human administration. In general, antioxidants maintain the radionuclide in its reduced state, while challenging agents form complexes with unbound or loosely bound metals that may facilitate oxidation, e.g. $Fe^{+3}/Fe^{+2}$. Enhanced stability has been observed when a stabilizing agent is contained in the eluate used during purification of the therapeutic preparation.

Ascorbic acid is a preferred stabilizing agent. Human serum albumin (HSA) may also be incorporated in the stabilizing agents of the present invention. Stabilizing agents comprising HSA in combination with an antioxidant or a challenging agent provide long term stabilization of therapeutic radionuclide compositions for up to a day or more.

It is unexpected, in view of the known or anticipated properties of radioactive rhenium compounds, that stabilizing agents such as ascorbic acid, alone or in combination with other stabilizing agents, would provide long-term stabilization of therapeutic radionuclide compositions. Use of the stabilizing agents of the present invention precludes the necessity of adopting more stringent stabilization measures, such as performing the conjugation and/or purification under anaerobic conditions and using the preparation immediately after purification. The stabilizing agents of the present invention effectively reduce decomposition of therapeutic radionuclide compositions which may be attributed to the reoxidation of the radioactive constituent (e.g. $^{186}$Re, $^{188}$Re), and to the effects of radiolysis. Long-term in vitro stability of from several hours to several days is provided by the stabilizing agents of the present invention and should enhance the availability and efficacy of therapeutic preparations, while reducing the toxic effects on normal, non-target cells and tissues.

DESCRIPTION OF PREFERRED EMBODIMENTS

The stable therapeutic radionuclide compositions of the present invention comprise a variety of radiolabeled compositions. Radio-immunoconjugates represent one preferred class of compositions wherein a therapeutic radioactive moiety is linked to a proteinaceous targeting moiety having specificity for certain target cells and/or tissue(s). Therapeutic radionuclides contemplated for use in the compositions of the present invention include beta (and gamma) emitting radionuclides such as $^{186}$Re, $^{188}$Re, $^{153}$Sm, $^{90}$Y, $^{105}$Rh, $^{131}$I, and the like. There is also some evidence that radioisotopes of the lanthanide series may exert therapeutic effects and may be suitable for use in the therapeutic radionuclide compositions of the present invention. Reduced rhenium radionuclides including $^{186}$Re and $^{188}$Re having an oxidation state of less than +7 are preferred for use in the therapeutic compositions of the present invention.

Suitable targeting moieties for incorporation in the therapeutic radionuclide compositions of the present invention include targeting moieties comprising proteins and polypeptides which may include carbohydrate moieties such as polysaccharides, glycoproteins, or other compounds having a carbohydrate moiety. Preferred proteinaceous targeting agents include antibodies, receptors (particularly cell surface receptors such as lectins), enzymes (e.g., fibrinolytic enzymes), biologic response modifiers (e.g., interleukins, interferons, lymphokines, erythropoietin, growth factors, colony stimulating factors, and the like), peptide hormones, and fragments thereof. Microaggregated proteins, such as microaggregated albumin (MAA) and the like, may also be used as targeting moieties. Monoclonal antibodies or fragments thereof are especially preferred proteinaceous targeting moieties. Among the many such monoclonal antibodies that may be used are anti-TAC, or other interleukin-2 receptor antibodies; 9.2.27 and NRML-05 to the 250 kilodalton human melanoma-associated proteoglycan; NRLU-10 to 37–40 kilodalton pancarcinoma glycoprotein; NRCO-02 having colon specificity; and OVB-3 to an as yet unidentified tumor-associated antigen. Numerous antibodies which are known or have not yet been isolated are also suitable for use in the present invention. Antibodies derived from hybridomas or by means of genetic or protein engineering techniques may be employed.

The targeting moieties may be modified as desired, as long as the biological activity necessary for the intended therapeutic application is retained. For example, chimeric antibodies which are produced by recombinant DNA techniques and have specificity determining portions derived from non-human sources and other portions derived from human sources, may be conjugated to therapeutic radioactive materials to provide radio-immunoconjugates according to the present invention. Antibodies employed in the present invention may comprise intact molecules, fragments thereof, or functional equivalents thereof. Exemplary antibody fragments include F(ab')$_2$, Fab', Fab and Fv fragments, which may be produced by conventional methods, or by genetic or protein engineering techniques. Engineered antibodies referred to as single chain antibodies may also be used.

Radio-immunoconjugates comprising rhenium radionuclides are typically produced by stably binding the radionuclide in a chelating agent, and subsequently coupling a portion of the radionuclide metal chelate to a proteinaceous targeting moiety. Numerous metal chelating agents are known in the art for chelating diagnostic agents such as $^{99m}$Tc and many of these agents are suitable for chelating therapeutic radionuclides such as $^{186}$Re and $^{188}$Re as well. Metal chelating compounds having nitrogen and sulfur donor atoms, such as dithiodiaminocarboxylic acids and dithiodiamidocarboxylic acids (known as N$_2$S$_2$ chelating agents), and thiotriaza chelating compounds (known as N$_3$S chelating agents), are preferred. Chelating compounds having the following general formulae are preferred:

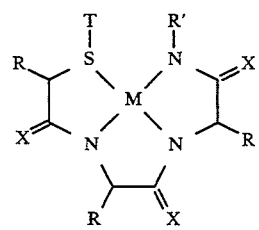

wherein:

T is H or a sulfur protecting group;

each x independently represents H$_2$ or O;

M is a radionuclide ion, to which 1 or 2 oxygen atoms may be bonded;

each R independently represents a substituent selected from the group consisting of hydrogen; alkyl; geminal dialkyl; a non-alkyl side chain of an amino acid other than cysteine (alkyl side chains being covered when R is an alkyl group); and —(CH$_2$)$_n$—Z;

Z represents —COOH, a conjugation group, or a targeting compound;

n is an integer of from 1 to about 4;

R' is H$_2$; —(CH$_2$)$_n$—Z; or an alkyl group having one or more polar groups substituted thereon; and the compound comprises at least one —$(CH_2)_n$—Z substituent wherein Z is a conjugation group or a targeting compound.

The conjugation group is a functional group which reacts with a group on the desired targeting moiety to bind the radionuclide metal chelate to the targeting agent. Proteinaceous targeting moieties contain a variety of functional groups such as carboxylic acid (—COOH) or free amine (—$NH_2$) groups, which are available for reaction with a suitable conjugation group on a chelating agent. For example, an active ester on the chelating agent reacts with free amine groups on lysine residues of proteins to form amide bonds. Alternatively, the protein and/or chelating agent may be derivatized to expose or attach additional reactive functional groups. The derivatization may involve attachment of any of a number of linker molecules. Alternatively, the derivatization may involve chemical treatment of the protein to generate, for example, free sulfhydryl groups which are reactive with maleimide conjugation groups on a chelating agent.

Among the preferred conjugation groups for reaction with proteinaceous targeting agents are esters. The esters which may be utilized as conjugation groups represented by "Z" are those esters which provide a covalent, amide linkage with a polypeptide in an aqueous medium. One or another of the reactive esters may be preferred, depending upon the particular radionuclide, the protein, and the conditions for conjugation, as is understood in the art of peptide chemistry. Common esters which find use are o- and p- nitrophenyl, 2-chloro-4-nitrophenyl, cyanomethyl, 2-mercaptopyridyl, hydroxybenztriazol, N-hydroxy succinimide, trichlorophenyl, tetrafluorophenyl, thiophenyl, tetrafluorothiophenyl, o-nitro-p-sulfophenyl, N-hydroxy phthalimide, and the like.

Alternatively, when the targeting agent has a carbohydrate moiety, derivatization may involve chemical treatment of the carbohydrate, such as glycol cleavage of the sugar moiety of a glycoprotein antibody with periodate to generate free aldehyde groups. The free aldehyde groups on the antibody may be reacted with free amine or hydrazine conjugation groups on the chelating agent to bind the radionuclide metal chelate thereto.

Suitable metal chelating agents are disclosed in European Patent Office Publication Numbers 0 188 256 and 0 284 071, as well as U.S. patent application Ser. No. 07/367,502 filed Jun. 16, 1989, which are incorporated by reference herein in their entireties. Other metal chelating agents which are known in the art are also suitable for use in the therapeutic radionuclide compositions of the present invention.

The chelating compound is radiolabeled to form the corresponding radionuclide metal chelate, and the chelate subsequently is attached to the targeting moiety in the "preformed chelate approach". An alternative approach to preparing radiolabeled targeting moieties is the "post-formed chelate approach", wherein the chelating compound is first attached to the protein or carbohydrate targeting molecule. The resulting conjugate is then reacted with a radionuclide metal to form a radionuclide metal chelate bound to the targeting molecule.

Preparation of radio-labeled rhenium immunoconjugates is described below. Depending upon the therapeutic radionuclide employed, various techniques may be utilized to prepare the radionuclide metal chelate. Perrhenate ($ReO_4^-$) is typically reduced to $ReO^{3+}$, $ReO_2^+$, or the like, prior to reaction with the chelating agent. In one embodiment of the invention, perrhenate may be reduced by reaction with stannous compounds or the like, and reacted with a transfer agent, such as citric acid, to form a weak rhenium citrate complex. The reduced rhenium radionuclide citrate complex is then reacted with a chelating agent, and the radionuclide is transferred to the ligand (chelating agent). This reaction produces a radionuclide chelate intermediate having an active ester moiety, or another conjugation group.

After the chelating reaction is complete, a buffer (pH 9.5 to 10) is introduced to elevate the pH of the chelated radionuclide solution. A buffered solution of the targeting moiety is then admixed with the chelated radionuclide. The active ester moiety of the radionuclide metal chelate intermediate is typically linked to a lysine residue of a proteinaceous targeting agent by means of an amide bond, but other types of linkages may also be used.

After the conjugation reaction is complete, the radionuclide compositions are purified to remove unreacted components, undesired reaction by-products, and decomposition products. A variety of purification techniques may be employed, including techniques such as gel permeation columns, which provide separation based upon molecular weight, and ion exchange chromatography, such as QAE anion exchange, which provides separation based upon charge characteristics.

Although preferred embodiments of the present invention have been described with reference to radioimmunoconjugates comprising rhenium radionuclide chelates linked to antibodies, other types of targeting moieties may be employed in the stable therapeutic radionuclide compositions of the present invention. Therapeutic radionuclides may be linked to other proteinaceous targeting moieties using technology which is known in the art. Chelating agents and/or known linker molecules may be used to link radionuclides to other targeting agents, or direct labeling techniques may be employed.

Radio-immunoconjugates comprising radio-halogen labeled targeting agents are typically produced by radio-labeling small molecules and subsequently binding the radio-halogenated small molecules to proteinaceous targeting agents. For example, the therapeutic radionuclide $^{131}I$ is preferably incorporated into a small molecule having the formula *X—Ar—R, wherein *X is a radiohalogen ($^{131}I$); Ar is an aromatic or heteroaromatic ring; and R is a short-chain substituent that does not highly activate ring Ar onto which the radiohalogen is substituted, and that bears a functional group suitable for conjugation to proteinaceous targeting moieties under mild, e.g., acylation, conditions that preserve the biological activity of the proteinaceous targeting agent. Preferred Ar rings include benzene, pyridine, furan and thiophene. The radiohalogen *X is preferably para- or meta-positioned on the Ar ring relative to substituent R to render the radio-halogen less susceptible to catabolism by dehalogenase enzymes. Attachment of the radiohalogen to a carbon atom in the Ar ring is preferred over attachment to an alkyl carbon atom due to the increased bond strength of the carbon-halogen bond in the aromatic or heteroaromatic ring. The nature of the Ar ring is not critical, and it may be mono-, bi-, tricyclic or contain a higher number of rings, but a monocyclic ring is preferred. Ring Ar may consist of all carbon atoms, or it may contain heteroatoms such as nitrogen, oxygen or sulfur. Further substitution on the Ar ring, exclusive of *X and R, with polar substituents such as a nitro, sulfonic acid, carboxylic acid, or dialkyl amino group may be preferred to enhance solubility in aqueous solutions.

The symbol "R" indicates any substituent that meets the following requirements. First, the R substituent must not highly activate ring Ar toward electrophilic substitution. In other words, R cannot be a substituent that, when bound to Ar, increases the electron density of Ar on the order of the increase produced by a free hydroxy or primary amino substitution. Second, R should be a short-chain substituent so that unconjugated or cleaved radiohalogenated molecules can be rapidly removed by the kidneys. Thus, R may contain an alkyl or other spacer chain between the aryl linkage and the functional group for protein conjugation, but such a spacer chain should preferably contain no more than 5, and most preferably no more than 3, straight-chain carbon atoms. Third, the R substituent should bear a functional group (termed "Q" herein) that is available for covalent attachment to corresponding functional groups (or conjugated attachment sites) on amino acid or carbohydrate residues of proteins, glycoproteins, or other proteinaceous targeting moieties under mild conjugation conditions. Representative R substituents include imide ester, alkyl imide esters, amido alkyl imide esters, imidate ester, alkyl imidate esters, and amido alkyl imidate esters.

Suitable functional groups Q for conjugation to proteinaceous moieties include phenolic esters (e.g., paranitrophenol), imide esters (e.g., succinimide ester), imidate esters, anhydrides, acylsuccinimides, aldehydes, isothiocyanates, thiol, diazo, amines, hydrazines, alkyl halides, Michael acceptor $\alpha,\beta$-unsaturated carbonyl compounds such as maleimides, and other groups that can be used to attach the molecule to a protein through a covalent bond. Also provided are radiohalogenated small molecules of formula I wherein the R substituent bears a precursor of functional group Q. Suitable precursors include: carboxylic acid where Q is phenolic ester, imide ester, anhydride, acylsuccinimide, or maleimide; nitrile where Q is imidate ester; alcohol where Q is aldehyde; halide where Q is isothiocyanate, thiol, hydrazine, or amine; and amine where Q is diazo or maleimide.

Representative radiohalogenated small molecules of this invention include the compounds having the following formulae:

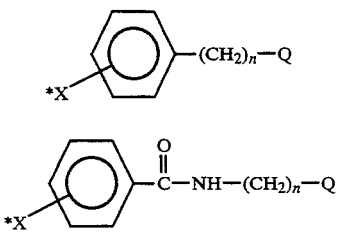

wherein:
*X is a radiohalogen, such as $^{131}I$;
n is an integer; and
Q is a functional group as stated above.

The radiohalogen may be positioned anywhere on the aromatic ring Ar, but para- or meta-substitution is preferred in order to make the radiohalogen less susceptible to steric instability and catabolism by deiodinase enzymes. The spacer component $(CH_2)_n$ can be a straight- or branched-chain alkyl or heteroalkyl group containing up to 12 but preferably no more than 5 straight-chain carbon atoms. In the most preferred embodiments no more than three straight-chain carbon atoms separate functional group Q from the aromatic ring; i.e., n=0,1,2, or 3. In order to quickly clear background activity for diagnostic imaging, and to minimize radiation dose to vital organs, the alkyl spacer component should be shortened so that nonconjugated and chemically or enzymatically cleaved radiohalogenated compounds can be rapidly cleared through the kidneys, rather than via fatty acid degradation pathways in the heart or liver. On the other hand, for certain applications a short alkyl or heteroalkyl spacer between the radiolabeled aryl ring and the protein may be desirable.

Illustrative but nonlimiting examples of radiohalogenated small molecules of this invention include: N-succinimidyl 3-(4'-[$^{131}I$]iodophenyl)-propionate; methyl 3-(4'-[$^{131}I$]iodophenyl)propioimidate; N-succinimidyl 4-[$^{131}I$]iodobenzoate; methyl 4-[$^{131}I$]iodobenzimidate; N-succinimidyl 4-[$^{131}I$]iodobenzamidoacetate or N-succinimidyl 4-[$^{131}I$]iodohippurate; methyl 4-[$^{131}I$]iodobenzamidoacetimidate; and 4-[$^{131}I$]iodobenzamidoacetonitrile.

Methods for synthesizing compounds having the formula *X—Ar—R are also provided. Briefly stated, the methodology described below may be used to metalate any positional isomer of a haloaromatic derivative bearing a functional group Q or a precursor to a functional group Q. The metalation will employ a trialkyltin reagent such as $Sn(n-Bu)_3$ or $SnMe_3$. The resulting aryltin compound can be transmetalated in a site-specific reaction with one of the following organomercury or organoboron reagents: $HgX_2$, $Hg(OAc)_2$, $BX_3$, or $BZ_3$, wherein X is Br,I, or preferably Cl, and Z is alkyl or alkoxy. The stannylated or otherwise metalated compound is radiohalogenated via a demetalation reaction, preferably after functional group Q is formed.

Radiohalogenated small molecules for binding to proteinaceous agents are described in European Patent Application Publication Nos. 0 203 764 and 0 289 187, which are incorporated by reference herein in their entireties.

Vinyl radiohalogenated small molecules having the following formulae may also be linked to proteinaceous targeting agents:

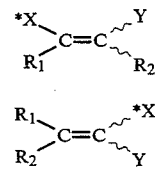

wherein:
*X is a radiohalogen, such as $^{131}I$;
C=C is a double bond;
$R_1$ and $R_2$ represent a hydrogen atom, alkyl or substituted alkyl group; an aryl or substituted aryl group; a heteroalkyl group; a heteroaryl group; or a mixed alkyl-aryl group; and
Y represents any of the groups as for $R_1$ and $R_2$, except that Y cannot be hydrogen, and bears a functional group suitable for binding to protein under conditions that preserve the biological activity of the protein.

These compounds can be coupled to proteins such as monoclonal antibodies as described above to provide reagents for diagnostic and therapeutic applications.

Stabilizing agents are introduced into the therapeutic radionuclide compositions of the present invention. Suitable stabilizing agents include, generally, antioxidants and challenging agents which are suitable for in vivo human administration. Stabilizing agents comprising antioxidants such as ascorbic acid, gentisic acid, reductic acid, derivatives thereof, such as nicotinamide complexes thereof, and functionally similar compounds; challenging agents such as DTPA, EDTA, and the like; and pharmaceutically acceptable salts, esters, amides, and mixtures thereof, are preferred stabilizing agents. Ascorbic acid is an especially preferred stabilizing agent since it is readily available at suitably high purity levels; it is acceptable for in vivo administration over a wide range of concentrations; it does not react chemically or physically with therapeutic radiolabeled compounds; and it demonstrates a high level of stabilizing activity.

The stable compositions of the present invention comprise an "effective amount" of a stabilizing agent, which represents an amount of stabilizing agent sufficient to maintain the therapeutic radionuclide in a reduced state and stably bound to the proteinaceous targeting moiety. Typically, therapeutic radionuclide compositions comprising radio-immunoconjugates are injected into human patients in a volume of about 20–30 ml. Such patient preparations preferably comprise from about 1 mg/ml to about 15 mg/ml stabilizing agent, e.g., antioxidant or challenging agent, and most preferably about 7–10 mg/ml stabilizing agent. The total amount of stabilizing agent in each radionuclide patient preparation is therefore from about 20 mg to about 500 mg, and preferably from about 120 mg to about 300 mg. In general, the amount of stabilizing agent required to provide the desired stability increases as the mass and the activity of the radionuclide increase.

Stabilizing agents of the present invention may be added to the therapeutic radionuclide composition after purification. According to preferred embodiments, however, the purification column is conditioned with an aqueous solution comprising the stabilizing agent prior to elution of the radionuclide composition, and the purified product is eluted with a solution comprising the stabilizing agent. In general, aqueous ascorbic acid solutions at concentrations of about 1 mg/ml or more, and preferably about 20 mg/ml, are preferred for conditioning and eluting the purification column. Aqueous solutions of DTPA and EDTA are likewise preferably provided at concentrations of up to about 20 mg/ml for column conditioning and elution.

In addition to the stabilizing agents described above, enhanced long term stability is provided when human serum albumin (HSA) is used in combination with one or more of the above-mentioned stabilizing agents. Experimental studies have demonstrated that the combination of HSA with an antioxidant or challenging agent induces an enhanced stabilizing effect. HSA, like ascorbic acid, is readily available at sufficiently high purity levels; it does not react with the therapeutic radionuclide compounds; and it may be administered in vivo to human patients over a wide range of dosage levels. Dosage levels of from about 50 mg to about 500 mg per patient preparation, and preferably about 220 mg, are preferred. HSA is preferably admixed with the radionuclide composition after purification.

The therapeutic radionuclide compositions of the present invention are intended for injection into humans or other mammalian hosts. Accordingly, appropriate manufacturing and in vitro storage practices must be observed to provide suitable sterile, pyrogen-free compositions. Although not necessary, it is preferable to use a pharmaceutically acceptable extender or filler to dilute the stabilizer and the (optional) carrier to simplify metering the requisite small quantities of such compounds. Sodium chloride and glucose are preferred carriers; sodium chloride is especially preferred because it facilitates provision of an isotonic solution.

Stable therapeutic radionuclide compositions according to the present invention may be diluted as necessary and administered to mammalian hosts by injection, intravenously, intraarterially, peritoneally, intratumorally, or the like, depending upon a variety of circumstances. Therapeutic $^{186}$Re compositions suitable for in vivo administration preferably have radioactivity levels of about 25 to about 600 mCi activity, and typically about 100 to about 300 mCi activity. Therapeutic compositions prepared for in vivo patient treatment preferably have relatively high specific activities with respect to the targeting moieties, generally antibodies (Ab) or fragments, of about 4 $\mu$Ci/$\mu$g Ab to about 8 $\mu$Ci/$\mu$g Ab. The level of radioactivity and the specific activity of preparations desirably administered to a patient will depend upon numerous factors, including the targeting moiety, the physical characteristics and health of the patient, the condition being treated, and the like.

The purity of the eluted therapeutic radionuclide composition must be determined prior to administration to a patient to confirm that the purity level is pharmaceutically acceptable. Purity measurements may be determined by a variety of techniques, including instant thin layer chromatography (ITLC) and high pressure liquid chromatography (HPLC). ITLC using a 12% TCA solvent is preferred for rapid determinations, and it provides an accurate measurement of the percentage of rhenium complexed and bound to antibodies or other targeting moieties in solution. HPLC with Zorbax diol using 0.2M phosphate buffer at pH 7 as the mobile phase may be used for identifying impurities and decomposition products and verifying purity levels.

The following description of experimental protocols and results illustrates radiolabeling and conjugation techniques linking rhenium radionuclides to antibodies to provide therapeutic radionuclide compositions and stabilization of those compositions. It is not intended to limit the invention, but rather, to describe specific experimental protocols and results for the purposes of supporting the claims of this application.

Radiolabeling and Conjugation Techniques for $^{186}$Re

Preparation of $^{186}$Re radionuclide compositions for clinical therapeutic applications involves several process steps: (1) formation of the $^{186}$Re ligand ester; (2) conjugation of the $^{186}$Re ligand ester to the targeting moiety; (3) purification of the $^{186}$Re reaction mixture; and (4) final dilution and testing prior to patient administration. All procedures involving manipulation of radionuclides should be carried out in a suitably shielded environment, such as a laminar flow hood shielded with clear lead glass bricks, lead bricks, and a lead sheet to reduce radiation exposure during the radiolabeling process. In addition, since the preparation is intended for in vivo administration, strict aseptic techniques must be observed.

$^{186}$Re in the form of soluble perrhenate ($^{186}$ReO$_4{}^-$) having the desired activity, generally from about 50 mCi to about 800 mCi, and having a mass of from about 0.01 to about 0.3 mg, is transferred to a reaction vial. Soluble perrhenate ($^{186}$ReO$_4{}^-$) may be obtained from the University of Missouri Research Reactor. The soluble perrhenate is reacted with a transfer agent composition comprising about 1 mg stannous chloride; 25 mg citric acid; 1 mg gentisic acid; and 75 mg lactose. The ratio of stannous chloride reducing agent:rhenium is from about 1:1 to about 10:1 on a molar basis to provide effective reduction, and the ratio of citric acid:rhenium is from about 25:1 to about 500:1 to efficiently generate the citrate/rhenium intermediate. The chelating agent is dissolved in an organic solvent such as isopropanol, and is introduced in quantities of from about 250 μg to about 800 μg to achieve $^{186}$Re:chelating agent offering ratios of about 1:1 to about 1:1.5, preferably about 1:1.3. The chelate reaction mixture is heated to 85°–95° C., and the reaction proceeds for about 30 minutes. The desired product of the chelating reaction is a chelated radionuclide ($^{186}$Re) having an active ester moiety.

One preferred chelating agent for rhenium radionculide composition is referred to as MAGG-GABA and has the following structure in the chelated, active ester form:

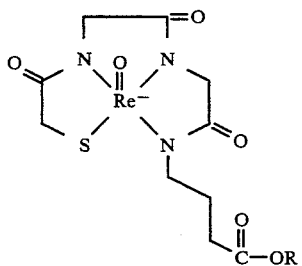

Ester purity of the reaction mixture may be quantified by chromatographic techniques.

The active ester moiety of the chelated radionuclide is then conjugated to a lysine residue of the proteinaceous targeting moiety. About 100 μl sodium carbonate buffer (1M, pH=10.0) is introduced to the $^{186}$Re-ligand ester reaction mixture, and an aqueous solution of the targeting moiety (typically whole or fragmented antibodies) is introduced to provide a rhenium:antibody offering ratio of about 0.1:1 to about 25:1, preferably about 2:1 to about 5:1. Additional carbonate buffer may be introduced to elevate the pH of the conjugation reaction mixture to about 9.0–9.5. The conjugation reaction proceeds for about 10 to about 12 minutes at room temperature with continuous stirring. 50 μl lysine (250 μl/ml) may be added (optionally) to quench the conjugation reaction. The reaction mixture is then purified by size exclusion using, for example, Sephadex G-25 columns, or by ion exchange chromotography. To provide stable radionuclide compositions according to preferred embodiments of the present invention, the purification column is preconditioned with aqueous solution comprising a stabilizing agent, and stabilizing solution is preferably used for elution of the purified radionuclide conjugates. The conjugation reaction mixture is diluted as necessary, for patient administration, or it may be divided into several portions for testing purposes.

EXAMPLE I

The in vitro stability of $^{186}$Re-MAGG-GABA-NRCO-02 F(ab')$_2$ radio-immunoconjugate preparations was monitored over time. Two radio-immunoconjugate preparations were made using the standard radiolabeling and conjugation techniques described above. Each radio-labeled immunoconjugate preparation was eluted using a PBS solution, and the purified eluted conjugate was collected in a vial containing a 5% solution of HSA (about 220 mg HSA) as a stabilizing agent. The total activity in Preparation I was about 25 mCi, and the total activity in Preparation II was about 100 mCi. Preparation I was divided into two groups, with one sample purified, collected and stored at 4° C., and the other sample purified, collected and stored at 37° C., to determine whether temperature influences the rate of decomposition of radio-immunoconjugates.

Stability of the radionuclide preparation was measured at various time intervals to monitor the purity level of the preparation. Stability was measured by ITLC (12% TCA solvent), as the percentage of radioactivity remaining bound in radio-immunoconjugate complexes. Purity levels below about 90%, and preferably below about 95%, are unacceptable for in vivo administration. Results are presented below:

| RADIO-IMMUNOCONJUGATE PURITY $^{186}$Re-MAGG-GABA-NRCO-02 F(ab')$_2$ | | | | |
|---|---|---|---|---|
| Preparation I = 25 mCi | | | Preparation II = 100 mCi | |
| Time | 4° C. | 37° C. | Time | 37° C. |
| T = 5 hrs | 99.0% | 99.1 | T = 0 | 96.0 |
| T = 7 hrs | 99.1 | 98.8 | T = 4 hrs | 89.4 |
| T = 9 hrs | 96.9 | 95.2 | T = 8 hrs | 87.0 |
| T = 11 hrs | 97.1 | 96.5 | T = 24 hrs | 76.8 |
| T = 27 hrs | 95.6 | 90.1 | T = 48 hrs | 67.3 |
| T = 51 hrs | 88.6 | 89.7 | T = 72 hrs | 59.3 |

The results demonstrate that radioimmunoconjugate preparations having higher levels of radioactivity are significantly less stable over time. Preparation I (25 mCi) demonstrated satisfactory stability for time periods of up to about 24 hours, while Preparation II (100 mCi) demonstrated satisfactory stability for only about 4 hours. No significant differences were observed between preparations purified, collected and stored at 4° C. and 37° C. HSA provides satisfactory stabilization at low radioactivity levels, but radionuclide compositions having a moderate level of activity (100 mCi) did not exhibit satisfactory stability. In general, higher total and specific activity preparations present more serious decomposition problems.

EXAMPLE II

In vitro stability of $^{186}$Re-MAGG-GABA-NR2AD radio-immunoconjugates was measured over time. NR2AD is a non-target specific (irrelevant) monoclonal antibody. The total (initial) preparation activity was about 137 mCi, and a $^{186}$Re:Ab offering of 2.67:1 produced conjugates having a specific activity of 6.0 μCi/μg Ab. The preparation was made using the standard radiolabeling and conjugation techniques described above. The conjugation reaction mixture was divided into three samples and purified on PD-10 columns.

Preparation I was the control preparation, wherein the radio-immunoconjugate mixture was eluted with PBS, and no stabilizing agent was employed. Preparation II employed 1.0 mg/ml ascorbic acid as a stabilizer which was used for both column conditioning and elution of the purified radionuclide conjugates. Preparation III employed 20 mg/ml ascorbic acid solution for column conditioning and elution of the purified conjugates. In addition, Preparation IV was prepared separately and purified under conditions similar to those of Preparation III, but 220 mg HSA was additionally provided in the collection vial. Results are tabulated below:

| RADIO-IMMUNOCONJUGATE PURITY $^{186}$Re MAGG-GABA-NR2AD | | | | |
|---|---|---|---|---|
| Time | Prep I | Prep II | Prep III | Prep IV |
| T = 0 | 93.6% | 95.6% | 98.5% | 99.5% |
| T = 1 | 87.8% | 95.5% | 98.4% | |
| T = 2 | 84.2% | 95.1% | 98.0% | |
| T = 4 | 75.6% | 94.2% | 97.8% | |
| T = 18 | 37.3% | 90.4% | 95.4% | 98.7% |
| T = 96 | 7.2% | 77.8% | 87.6% | 95.5% |

These experimental results indicate that higher concentrations of ascorbic acid (20 mg/ml compared to 1 mg/ml) provide enhanced stabilizing effects, and that the combination of ascorbic acid and HSA provides an enhanced long-term stabilization effect. A stabilizing solution comprising 1 mg/ml ascorbic acid used to condition the purification column and as a column eluate provides satisfactory stability for up to about 18 hours. The twenty-fold higher concentration of ascorbic acid used in Preparation III provides significantly improved stability compared to preparations I and II, and the 20 mg/ml ascorbic acid/220 mg HSA stabilizer used in Preparation IV maintains greater than 95% radionuclide composition purity for at least 96 hours.

EXAMPLE III $^{186}$Re-MAGG-GABA-NRCO-02 F(ab')$_2$ radio-immunoconjugates having a relatively high specific activity were prepared according to the standard radiolabeling and conjugation techniques described above. The total (initial) preparation activity was about 216 mCi, and the specific activity was 7.3 μCi/μg Ab. The preparation was divided into two samples and was monitored to determine stability over time. Preparation I was a standard control preparation in which a stabilizer was not used and the conjugate reaction mixture was eluted with PBS, while Preparation II was analogous to Preparation IV described in Example II, above. Experimental results are shown below:

| RADIO-IMMUNOCONJUGATE PURITY $^{186}$Re-MAGG-GABA-NRCO-02 F(ab')$_2$ | | |
|---|---|---|
| Time (Hours) | Preparation I | Preparation II |
| T = 0 | 92.4% | 97.1% |
| T = 2 | 82.8% | 95.8% |
| T = 5 | 70.9% | 96.6% |
| T = 10 | 41.5% | 96.3% |
| T = 24 | 26.4% | 95.8% |
| T = 42 | 14.2% | 95.6% |
| T = 48 | 10.9% | 95.5% |
| T = 114 | | 93.8% |
| T = 142 | | 93.5% |

These experimental results confirm the observations reported in Example II, namely that a stabilization technique employing 20 mg/ml ascorbic acid solution for conditioning the purification column and eluting the radio-immunoconjugate mixture in combination with HSA provided in the collection vial, provides significantly enhanced long term stability. The control preparation, which contained no stabilizing element, exhibited only marginally acceptable purity immediately after purification. Long-term stability (nearly 6 days) of radio-labeled immunoconjugates was achieved at a high $^{186}$Re specific activity of 7.3 μCi/μg Ab.

EXAMPLE IV

The experiment reported in Example III was repeated to test the stability of $^{186}$Re-MAGG-GABA-NRLU-10 radio-immunoconjugates. The preparation had a specific activity of 8.2 μCi/μg Ab. The preparation was divided into two samples and Preparations I and II purified as described in Example III. Experimental results are shown below:

| RADIO-IMMUNOCONJUGATE PURITY $^{186}$Re-MAGG-GABA-NRLU-10 | | |
|---|---|---|
| Time (Hours) | Preparation I | Preparation II |
| T = 0.5 | 83.5% | 97.1% |
| T = 2 | 76.6% | 97.0% |
| T = 4 | 64.9% | 96.0% |
| T = 6 | 55.2% | 97.4% |
| T = 18 | 26.4% | 97.0% |
| T = 44 | 10.5% | 96.1% |
| T = 72 | | 95.6% |
| T = 120 | | 94.6% |
| T = 144 | | 94.2% |

Again, the stabilization technique employing 20 mg/ml ascorbic acid solution for preconditioning the purification column and eluting the radio-immunoconjugate reaction mixture in combination with HSA exhibited dramatically enhanced long-term stability for up to 6 days, and provided enhanced initial preparation purity. The results are especially significant in view of the high specific activity of the preparation.

EXAMPLE V

Three proposed stabilizers, ascorbic acid, gentisic acid, and DTPA, were tested under similar conditions to determine their efficacy for in vitro stabilization of radio-immunoconjugates. $^{186}$Re MAGG-GABA-NR2AD radio-immunoconjugates were prepared according to the standard radiolabeling and conjugation techniques described above. The preparation had an activity of about 5.1 μCi/μg Ab. Each purification column was treated with a conditioning solution containing the stabilizer, and the radio-immunoconjugate mixture was eluted using the stabilizer solution. The stabilizers used were as follows: Preparation I—20 mg/ml ascorbic acid; Preparation II—20 mg/ml gentisic acid; and Preparation III—20 mg/ml DTPA. Experimental results are shown below:

| RADIO-IMMUNOCONJUGATE PURITY $^{186}$Re-MAGG-GABA-NR2AD | | | |
|---|---|---|---|
| Time | Preparation I (Ascorbic Acid) | Preparation II (Gentisic Acid) | Preparation III (DTPA) |
| T = 0 | 95.7% | 97.8% | 98.3% |
| T = 2 | 94.7% | 97.5% | 96.5% |
| T = 4 | 97.7% | 97.5% | 95.5% |
| T = 21 | 97.3% | 93.4% | 84.3% |
| T = 25 | 93.7% | 91.9% | 82.3% |
| T = 48 | 95.9% | 85.0% | 72.7% |

-continued

RADIO-IMMUNOCONJUGATE PURITY
186Re-MAGG-GABA-NR2AD

| Time | Preparation I (Ascorbic Acid) | Preparation II (Gentisic Acid) | Preparation III (DTPA) |
|---|---|---|---|
| T = 144 | 91.2% | 56.1% | 52.8% |

These experimental results show that ascorbic acid consistently provides long-term stabilization, while gentisic acid provides satisfactory stabilization for about 24 hours. The DTPA preparation demonstrated satisfactory stability for only about 4 hours. Each of the stabilizers tested demonstrated a stabilizing effect compared to preparations in which the radio-immunoconjugate was eluted and stored with PBS. Ascorbic acid is the preferred long-term stabilizer.

EXAMPLE VI

Stabilization studies similar to those described in Example V were repeated to assess the effect of HSA on stabilizers, including ascorbic acid, gentisic acid, and DTPA. $^{186}$Re-MAGG-GABA-NRLU-10 radio-immunoconjugates were prepared according to the standard radio-labeling and conjugation techniques described above. The specific activity of the preparation was about 6.1 $\mu$Ci/$\mu$g Ab. The stabilizers used for preparations I, II and III were as described in Example V, with "A" series signifying that HSA (220 mg) was additionally provided in the collection vial. The "B" series indicates that HSA was not used. The results are shown below:

RADIO-IMMUNOCONJUGATE PURITY
186Re-MAGG-GABA-NRLU-10

| | Preparation I (Ascorbic Acid) | | Preparation II (Gentisic Acid) | | Preparation III (DTPA) | |
|---|---|---|---|---|---|---|
| Time | A (HSA) | B | A (HSA) | B | A (HSA) | B |
| T = 0 | | | 91.2% | 93.5% | | |
| T = 2 | 92.2% | 93.1% | 87.4% | 92.1% | 90.4% | |
| T = 4 | 92.2% | 92.3% | 88.6% | 85.4% | 87.2% | 90.1% |
| T = 21 | 92.1% | 91.7% | 86.7% | 88.6% | 90.5% | 90.1% |
| T = 24 | 91.7% | 90.6% | 85.6% | 86.7% | 88.3% | 87.1% |
| T = 44 | 91.1% | 90.0% | 85.8% | 79.8% | 88.5% | 88.7% |
| T = 80 | 91.2% | | 84.8% | | 86.9% | |
| T = 98 | 91.1% | 88.0% | 84.5% | 57.7% | 86.8% | 84.9% |
| T = 133 | 90.5% | 86.4% | 84.0% | 44.7% | 85.7% | 83.4% |
| T = 190 | 89.9% | 84.5% | 82.8% | 31.8% | 84.3% | 79.5% |

These results demonstrate that using HSA in combination with another stabilizer such as ascorbic acid, gentisic acid, or DTPA provides enhanced in vitro stabilization of radio-immunoconjugates.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

We claim:

1. A stable purified therapeutic radionuclide preparation suitable for in vivo administration comprising a therapeutic radionuclide selected from the group consisting of $^{186}$Re; $^{188}$Re; and mixtures thereof linked to a proteinaceous targeting moiety, the therapeutic radionuclide preparation also comprising an effective amount of a stabilizing agent comprising ascorbic acid, wherein the radiochemical purity of the therapeutic radionuclide preparation is maintained at a level of at least about 90% for at least about 4 hours.

2. A therapeutic radionuclide preparation according to claim 1, wherein the therapeutic radionuclide is $^{186}$Re and the preparation has a specific activity of about 4 $\mu$Ci/$\mu$g targeting agent to about 8 $\mu$Ci/$\mu$g targeting agent.

3. A therapeutic radionuclide preparation according to claim 1, comprising at least about 1 mg/ml stabilizing agent.

4. A therapeutic radionuclide preparation according to claim 1, comprising from about 20 to about 500 mg stabilizing agent.

5. A therapeutic radionuclide preparation according to claim 1, comprising from about 1 mg/ml to about 20 mg/ml ascorbic acid.

6. A therapeutic radionuclide preparation according to claim 1, wherein the proteinaceous targeting moiety comprises an antibody or an antibody fragment.

7. A therapeutic radionuclide preparation according to claim 1, comprising a rhenium radionuclide bound to a chelating agent to form a radionuclide metal chelate and a proteinaceous targeting moiety coupled to the radionuclide metal chelate.

8. A therapeutic radionuclide preparation according to claim 7, wherein the chelating agent is an $N_2S_2$ or an $N_3S$ chelating agent.

9. A therapeutic radionuclide preparation according to claim 8, wherein the chelating agent is MAGG-GABA.

10. A therapeutic radionuclide preparation comprising a rhenium radionuclide stably linked to a proteinaceous targeting moiety which retains at least about 90% radiochemical purity during in vitro storage periods of at least about 4 hours in the presence of a stabilizing agent comprising ascorbic acid.

11. A pharmaceutically acceptable preparation having therapeutic properties comprising: a therapeutic radionuclide selected from the group consisting of $^{186}$Re; $^{188}$Re; and mixtures thereof stably linked to a proteinaceous targeting moiety; an effective amount of stabilizing agent comprising ascorbic acid and a pharmaceutically acceptable carrier or diluent.

12. A method for therapeutic treatment of neoplastic diseases, comprising administering to a patient a therapeutically effective amount of the pharmaceutically acceptable preparation of claim 11.

* * * * *